US011589850B2

(12) United States Patent
Odintsov et al.

(10) Patent No.: US 11,589,850 B2
(45) Date of Patent: Feb. 28, 2023

(54) ASPIRATION SYRINGE

(71) Applicants:Vladislav Alexandrovich Odintsov, Saint Petersburg (RU); Mikhail Yurievich Levashov, Saint Petersburg (RU); Elena Yul'anovna Oreshchenko, Georgievsk (RU)

(72) Inventors: Vladislav Alexandrovich Odintsov, Saint Petersburg (RU); Mikhail Yurievich Levashov, Saint Petersburg (RU); Elena Yul'anovna Oreshchenko, Georgievsk (RU)

( * ) Notice: Subject to any disclaimer, the term of this patent is extended or adjusted under 35 U.S.C. 154(b) by 397 days.

(21) Appl. No.: 16/753,769

(22) PCT Filed: Dec. 5, 2018

(86) PCT No.: PCT/RU2018/050157
§ 371 (c)(1),
(2) Date: Apr. 4, 2020

(87) PCT Pub. No.: WO2019/070170
PCT Pub. Date: Apr. 11, 2019

(65) Prior Publication Data
US 2020/0268363 A1    Aug. 27, 2020

(30) Foreign Application Priority Data

Oct. 5, 2017    (RU) .......................... RU2017135551

(51) Int. Cl.
*A61B 10/02*    (2006.01)
*A61B 10/00*    (2006.01)

(52) U.S. Cl.
CPC ...... *A61B 10/0283* (2013.01); *A61B 10/0045* (2013.01)

(58) Field of Classification Search
CPC .......... A61B 10/0283; A61B 10/0045; A61M 5/3148
See application file for complete search history.

(56) References Cited

U.S. PATENT DOCUMENTS

| 2,585,815 | A | * | 2/1952 | McClintock | ...... | A61M 5/31595 604/209 |
| 3,797,487 | A | * | 3/1974 | Schmidt | .................. | A61M 5/24 604/232 |

(Continued)

FOREIGN PATENT DOCUMENTS

| CN | 107661125 A | * | 2/2018 |
| CN | 110151230 A | * | 8/2019 |

(Continued)

*Primary Examiner* — Sean P Dougherty
(74) *Attorney, Agent, or Firm* — Bayramoglu Law Offices LLC

(57) ABSTRACT

The invention relates to the field of medical equipment, more specifically to syringes, and can be used for procedures of aspiration of various fluids, for fine needle biopsy, for puncture morphological diagnostics, and for injections of liquid medicinal products. The subject matter of the invention: the disclosed device, including a barrel with a tip for attaching a needle at one end, a piston with a stem slidingly mounted inside the barrel, and a grip at the end of the stem, according to the invention, is provided with a handle moveably coupled to the stem grip and rotatable in relation to a hinge unit located on the stem grip, wherein the handle is at least formed as a bracket with a reverse grip located at the end opposite to the handle attachment and having a slot arranged in the middle portion and intended for enclosing the stem on two sides.

10 Claims, 2 Drawing Sheets

(56) References Cited

U.S. PATENT DOCUMENTS

| | | | |
|---|---|---|---|
| 3,990,446 A | | 11/1976 | Taylor |
| 4,216,771 A | * | 8/1980 | Arlers ................ A61M 5/31511 604/229 |
| 4,641,663 A | * | 2/1987 | Juhn ................ A61B 10/0045 141/27 |
| 5,498,246 A | | 3/1996 | Deutchman et al. |
| 5,582,595 A | | 12/1996 | Haber et al. |
| 5,651,372 A | | 7/1997 | Caillouette |
| 5,685,862 A | * | 11/1997 | Mahurkar ............. A61M 5/322 604/528 |
| 5,807,334 A | * | 9/1998 | Hodosh ................ A61M 5/482 604/224 |
| 6,231,550 B1 | | 5/2001 | Laughlin |
| 7,988,677 B2 | | 8/2011 | Fojtik |
| 9,067,023 B2 | * | 6/2015 | Bertocci ............. A61M 5/3148 |
| 2007/0265573 A1 | | 11/2007 | Fojtik |
| 2010/0152611 A1 | * | 6/2010 | Parihar ............. A61B 10/0275 600/566 |
| 2019/0275257 A1 | * | 9/2019 | Jordan ............... A61B 10/0283 |

FOREIGN PATENT DOCUMENTS

| | | | | |
|---|---|---|---|---|
| CN | 110477966 A | * | 11/2019 | |
| EA | 022706 B1 | | 2/2016 | |
| FR | 2609624 A | * | 7/1988 | ......... A61B 10/0045 |
| RU | 47745 U1 | | 9/2005 | |
| RU | 2266756 C2 | | 12/2005 | |
| RU | 68876 U1 | | 12/2007 | |
| RU | 115666 U1 | | 5/2012 | |
| WO | 9853867 A1 | | 12/1998 | |
| WO | WO-2013005881 A | * | 1/2013 | ......... A61B 10/0283 |

\* cited by examiner

ASPIRATION SYRINGE

CROSS REFERENCES TO THE RELATED APPLICATIONS

This application is the national phase entry of International Application No. PCT/RU2018/050157, filed on Dec. 5, 2018, which is based upon and claims priority to Russian Patent Application No. 2017135551, filed on Oct. 5, 2017, the entire contents of which are incorporated herein by reference.

TECHNICAL FIELD

The invention relates to the field of medical equipment, more specifically to syringes, and can be used for injecting liquid medicinal products into body tissues as well as for performing aspiration of contents of, for example, cystic formations, for fine needle biopsy, and for puncture morphological diagnostics of neoplasms of internal organs.

BACKGROUND

It is known that one of the essential requirements in performing medical procedures, such as injection, aspiration, and puncture, is to precisely insert a needle in the desired place in the patient's tissue and to prevent displacement of the needle during the procedure. Thus, a device used to perform the procedure should be comfortable for the operator, allow for physiological, natural movement of the fingers of the operating hand so as to prevent its overstrain. This requirement is particularly important if a doctor or a nurse needs to perform a medical procedure only with one hand, while holding a patient or another tool with the other hand. For these cases, there is a need in a device which can be handled with one hand without compromising the quality of performing the procedure.

From prior art is known an "Aspiration Cartridge Syringe with an Original Removable Adapter for Needles with a Passive Aspiration System" in accordance with Russian utility model patent 68876, IPC A61B 3/00, published Dec. 10, 2007. This cartridge syringe includes a body with a cartridge, a piston pusher with a finger grip, additional retention devices formed as a harpoon, notches, a screw, and a removable threaded adapter.

This device is characterized in that it has a removable adapter for needles with a passive aspiration system, the adapter being provided with a tubular pin located on the outer surface of the cylindrical sleeve of the removable adapter and extending into the inner space of the syringe body.

After the adapter has been screwed in and the cartridge has been mounted, the cartridge diaphragm is punctured by the needle. When the piston-seal is pushed, the tubular pin deforms the diaphragm, thus creating a positive pressure. When the pressure is taken off the pusher, the diaphragm straightens out and negative pressure builds in the cartridge, which results in aspiration of fluid from tissues.

This device is aimed at facilitating performing the aspiration by eliminating the need to pull back the piston and change the operator's hand position. However, before starting the procedure, the operator needs to make additional preparations, i.e., to mount the removable adapter and the cartridge on the syringe. Moreover, before inserting the needle, the piston in the barrel needs to be moved to the end position by pushing the piston, and when the needle enters the tissues the piston needs to be held in the pushed condition to maintain positive pressure in the syringe, which can cause undesired movements of the needle or piston and because of which the needle may not enter the desired spot, thus requiring its repeated insertion, which additionally traumatizes the patient.

This device allows performing a medical procedure with one hand, but it has a complex construction and requires additional preparations, as well as involves the operator performing several actions at a time, such as inserting the needle into the tissue and holding the syringe piston to maintain a positive pressure in the barrel, which significantly compromises the performance of the device.

A device "syringe for stabilized aspiration by one hand" is known from the patent U.S. Pat. No. 3,990,446, IPC A61M 1/00, A61M 5/31, published Sep. 11, 1976.

This device is a disposable hypodermic syringe for aspiration comprising a cylindrical thermoplastic barrel partially closed at one end and open at an opposite end, on which two flat transverse barrel flanges extend in opposite directions to stabilize the syringe. At the partially closed barrel end is an adapter to facilitate connecting a needle assembly. The barrel length is approximately twice the length of the plunger and stopper coupled together and axially slidable completely within the barrel. The end of the plunger shaft opposite the stopper end consists of a flat plate with two plunger flanges attached thereto. Both plunger flanges branch perpendicularly outward from the plate through opposing apertures cut through the lateral walls of the syringe barrel. The two opposing apertures are rectangular in shape and extend from a midpoint on the barrel to a point spaced just below the open end. The widths of both barrel apertures align with the widths of both barrel flanges. Before aspiration the plunger stopper rests against the partially closed end of the barrel, in which the two plunger flanges protrude outward through the barrel apertures near the midpoint of the barrels length. Aspiration by one hand is accomplished when the plunger flanges are drawn toward the barrel flanges, and the barrel flanges are stabilized against movement.

This device allows performing aspiration by one hand, and the movements of the fingers correspond to those of natural clenching of the hand, but the clenching movement of the fingers does not suffice. After inserting the needle into the tissue, the fingers holding the syringe should be moved to the plunger stem in order to displace the latter, which can cause undesirable movements of the syringe and displacement of the needle during the procedure traumatizing the patient.

Also, known is a device "single handed syringe-pump for aspiration, injection and fluid transfer" according to the patent U.S. Pat. No. 5,498,246, IPC A61B 10/00, A61B 10/02, A61B 17/44, A61M 5/178, published Mar. 12, 1996.

The device includes a closed loop at the remote end of the barrel and a piston with a handle for gripping with one hand, and also check valves located in a withdrawal duct and a drainage port, configured to prevent any fluid withdrawn from the body from being reinjected into the body cavity. Aspiration is performed by pulling the handle on the piston end by the fingers of the operating hand, wherein the piston rests on the spring and moves against its bias. The size of the handle on the piston end should correspond to the size of the operator's fingers. This device allows handling by one hand, wherein the movement of the operator's fingers corresponds to a natural clenching movement of the hand, but the closed loop limits the piston stroke, which can be insufficient for withdrawing all fluid intended for aspiration, because of which the procedure may have to be repeated. Moreover, the spring provided in the design of the device needs to be forcibly retained in the compressed condition until the needle is withdrawn from the tissue, otherwise its loosening leads to the withdrawn material reentering the tissue, which can result in hemorrhage. Said features of the device make its construction complex and its manufacture expensive, particularly in case of a single use, make the device harder for a medical worker to operate and increase the risk of traumatizing the patient.

Further, the patent U.S. Pat. No. 6,231,550, IPC A61M 5/31, published May 15, 2001, discloses a device "one-handed grip aspiration syringe".

The syringe has a barrel with wings, a piston, and a sleeve. The piston has a head configured for slidable engagement with the barrel, and a stem terminating in a grip at the free end of the piston. The syringe also has a sleeve encircling the barrel and engaged with the piston through a pinion gear, wherein the sleeve also has a stem. An operator activates the device by pressing the sleeve stem with the thumb of the operating hand. The force applied to the sleeve is transferred to the piston through the pinion gear and displaces the piston in the direction opposite to the applied force.

This device can be used in an injection mode or in an aspiration mode, while the user holds the syringe in one hand with the fingers in the same holding position, and in both modes, the device is activated by the operator advancing the thumb toward the fingers holding the syringe. However, the sleeve stem transferring force to the piston is located on one side from the syringe barrel, asymmetrically to it, which can slant the syringe piston and ultimately lead to its breakdown. With that, the pinion gear formed as geared surfaces on one side of the piston stem and on the inner surface of the sleeve can rapidly wear off resulting in the slippage of gears and, thus, in the intermittent motion of the piston, which is unacceptable in the medical procedure. Moreover, since the force applied by the thumb should be considerable to overcome friction in the pinion gear, it creates significant load on the joint and can cause pain in case of frequent use of such syringe, which decreases the ease of use and lowers the number of procedures administered.

A device "biopsy syringe" according to the patent U.S. Pat. No. 5,651,372, IPC A61B 10/02, published Jul. 29, 1997, taken as a prototype, is the closet prior art to the presently disclosed device in terms of technical essence.

The syringe assembly comprises a barrel with a tip for mounting a needle thereon, and a plunger with a stem, moveable within the barrel. The barrel is provided with a pair of rings designed for gripping with fingers and holding the device, located on the opposite sides thereof, and the plunger comprises a ring at the stem end, wherein the movement of the piston during the aspiration (puncture) procedure is accomplished by pulling back the thumb within the ring at the piston end, i.e., the plunger can be removed from the barrel with one hand. The syringe plunger stem comprises four longitudinal ribs forming a X-shaped cross-section, and plunger motion limiting means include a positioning knob on a plunger rib, with a stopper attached to it and moveably connected to the plunger.

This device can be used for performing an aspiration procedure while holding it in one hand. In addition, grip rings prevent fingers from slipping along the barrel when withdrawing the plunger.

However, retracting a thumb systematically and repeatedly in the direction away from the operator's hand is not physiological, heavily loads the joint and ligaments causing microtraumas in the latter, pain, and easy fatigue when performing the procedure. Also, the movement of plunger is limited by the length of the thumb of the operator's operational hand, so it is practically impossible to move the plunger to the topmost position. Consequently, the amount of material withdrawn through aspiration is also limited, which can result in the necessity to repeat the procedure. In addition, after the needle has been inserted it is required to move the fingers holding the syringe and place them into the rings, which can displace the needle and traumatize the patient. Furthermore, the rings restrict the freedom of handling the syringe by compressing blood vessels, cause finger numbness, which in turn leads to painful sensations and easy fatigue of the operator when performing a procedure, and, consequently, limits the number of procedures administered making this device less convenient and effective in operation.

The disclosed device eliminates the mentioned drawbacks.

SUMMARY

The invention solves the problem of creating a constructionally simple but reliable, safe, easy to use, and operationally effective tool for performing a procedure of withdrawing fluid material from the patient's body, in particular, for a procedure of aspiration, puncture or biopsy, which allows performing these procedures by one hand.

The technical effect obtained by using the invention is improved convenience of use of a syringe by the operator with one hand, improved reliability and lowered risk of trauma during the procedure of aspiration and other similar procedures, and improved performance due to the construction of the device, which allows handling it with one hand by advancing the thumb toward the fingers holding the syringe, which corresponds to a natural motion of clenching a hand and does not strain and injure the operating hand, and, consequently, allows to increase the number of procedures performed by a medical worker, wherein the need to change the position of the fingers of the operating hand is eliminated.

The technical effect is achieved by that the disclosed device, comprising: a barrel with a tip for attaching a needle at one end; a piston having a stem and slidably mounted inside the barrel; and a grip located at an end of the stem, further comprises a handle moveably attached to the stem grip and rotatable in relation to the hinge unit located at the stem grip, wherein the handle is formed at least as a bracket with a reverse grip located at the end opposite to the handle attachment and with a slot arranged in the middle portion and intended for enclosing the stem from two sides. In addition, the stem grip is formed as an elongated pad extending asymmetrically to the axis of symmetry of the stem, wherein the hinge unit is located on a bottom surface of the stem grip.

Furthermore, the bracket is arched, and the curvature radius of the bracket approximately equals the distance the piston exits the barrel in operation, the slot in the bracket extends along an entire length of the bracket, and the width of the slot corresponds to the diameter of the piston stem.

Furthermore, the handle can have an auxiliary bracket located on the bottom surface of the reverse grip. The auxiliary bracket is formed as at least one arched element having a slot arranged in the middle portion and intended for enclosing the barrel, and having a tab located at an end opposite to the reverse grip. Moreover, the width of the slot in the auxiliary bracket corresponds to the outer diameter of the barrel.

Furthermore, the auxiliary bracket can be formed as two arched elements of different diameters coupled to each other. Moreover, the slot of the auxiliary bracket is formed only in the second bracket element adjacent to the tab.

Furthermore, the arched elements of the auxiliary bracket and the tab are sized so as to correspond to the size of the fingers.

DETAILED DESCRIPTION OF THE EMBODIMENTS

Figure 1:
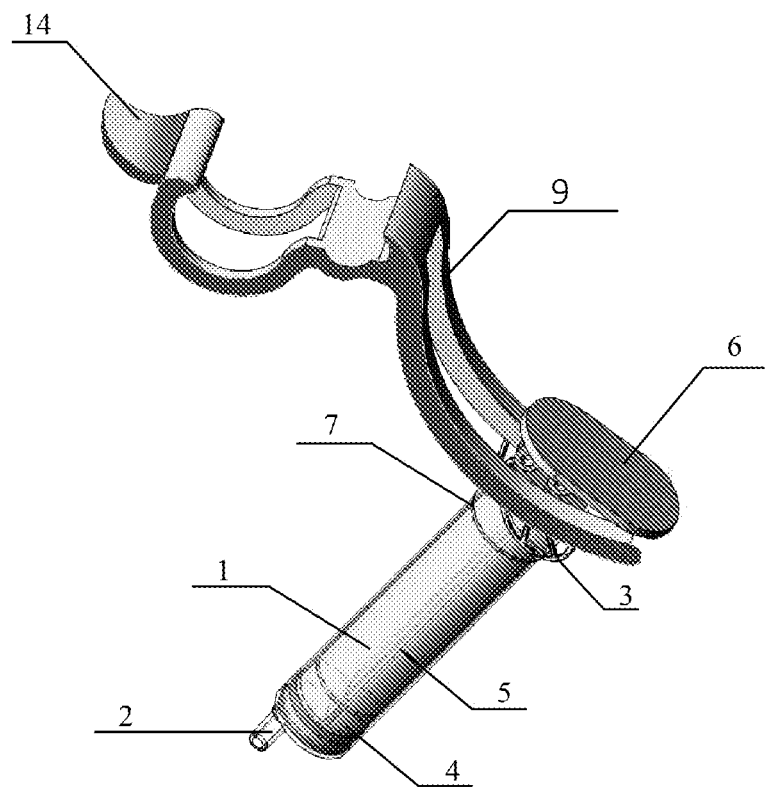
FIG. 1 shows a general view of a syringe before an aspiration begins.

The disclosed aspiration syringe (FIG. 1) has a barrel 1 with a tip 2 for mounting a needle at one end thereof and a flange 3 at the other end thereof. A piston 4 with a stem 5 is slidably mounted inside the barrel 1, and there is a finger grip 6 on its end configured to be engaged (pressed) in case of injecting medicinal substances into a patient's body.

The barrel 1 is made of polypropylene and has a stop ring (a fixing mechanism) 7 on its inner surface closer to the flange 3 to prevent the piston 4 from inadvertently slipping out of the barrel 1. A scale (not shown) that allows measuring the medical substance when making an injection or determining the volume of fluid withdrawn from the body during the procedure of aspiration (puncture), can be applied on the outer surface of the barrel 1 via engraving or with indelible paint.

The syringe piston 4 is made of high-density polyethylene, and its stem 5 is formed of four longitudinal ribs forming a X-shaped cross-section, which allows minimizing friction of the piston against the barrel 1 walls and keeping a symmetrical position in relation to the walls and the rigidity of the stem 5 at the same time.

The grip 6 mounted at the end of the stem 5 of the piston 4 can be flat or have a slightly concave shape for convenience of placing a doctor's or a nurse's thumb thereon when injecting a medical substance (injection). In contrast to the known analogues, the grip 6 is slightly elongated in one direction in relation to the axis of symmetry of the syringe stem, forming a protrusion having a hinge unit 8 on its bottom surface on that side, the moveable handle 9 actuated by the operator's operational thumb and the stem 5 being connected through the hinge unit.

Figure 2:
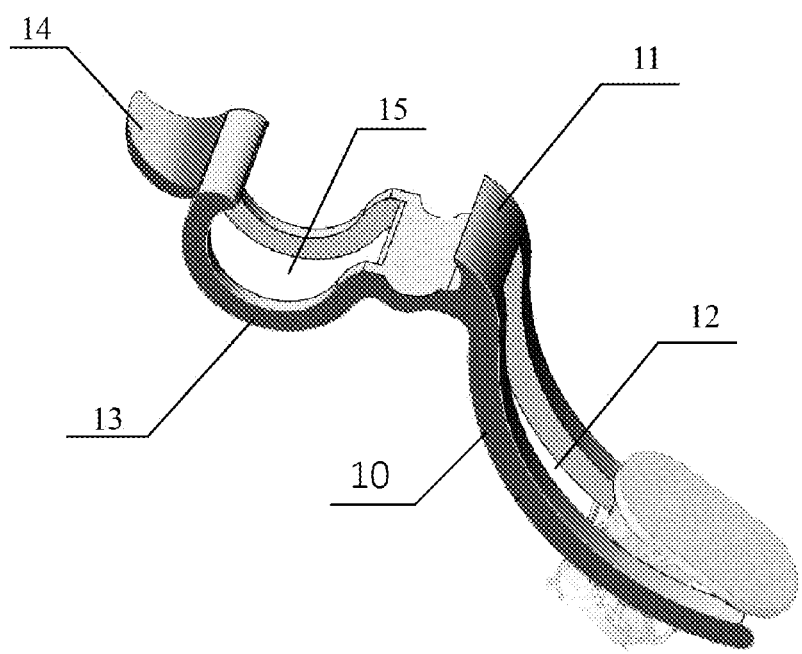
FIG. 2 shows a syringe handle.

The main element of the handle 9 (FIG. 2) is a bracket 10 formed as a segment of a circle and having a reverse grip 11 on an end thereof and a slot 12 arranged in the middle portion and intended for enclosing the stem 5 from two sides when it is moved upward (when performing aspiration). The arched shape of the bracket 10 allows increasing the stroke of the piston with a minimal operator's effort and at the same time shortens the distance from the grip 6 of the stem 5 to the reverse grip 11 of the bracket 10, consequently facilitating operator's access to the handle 9 engagement spot and eliminating the need to move the finger for a long distance. Experiments proved that the curvature radius of the bracket 10 approximately equals the distance the piston 4 exits the barrel 1 in operation before it rests on the stop ring 7.

The width of the slot 12 in the bracket 10 of the handle 9 should correspond to (be slightly greater than) the diameter of the piston stem 5. Similarly to the barrel 1 of the syringe, the handle 9 is also made of polypropylene.

In an embodiment of the device, in order to maximize the exit of fluid being withdrawn, the handle 9 can be provided with an auxiliary bracket 13 extending from the bottom surface of the reverse grip 11, and can be formed as at least one arched element having a tab 14 on its end and a slot 15 arranged in the middle portion and intended for enclosing the barrel 1 from two sides when the stem 5 is moved upward (when performing aspiration). Accordingly, the width of the slot 15 in the bracket 13 of the handle 9 should correspond to or be slightly greater than the outer diameter of the barrel 1.

In an optimal embodiment, the auxiliary bracket 13 is formed as two arched elements of different diameters coupled to each other, wherein the slot 15 is formed only in the second bracket 13 element adjacent to the tab 14. By alternatively pressing the elements of the auxiliary bracket 13 of the handle 9 with a finger, the piston 4 can be additionally extended in a step-wise manner. When the force is applied to the tab 14 the piston 4 moves to the topmost position exiting the barrel 1 for the maximum length of the stem.

Moreover, the concave elements of the auxiliary bracket 13 and the tab 14 are sized so as to correspond to the fingers providing for additional convenience of using the syringe and improving the effectiveness of its handling. In addition, by actuating the reverse grip 11 of the handle 9, the elements of the auxiliary bracket 13, and the tab 14 in a step-wise manner, the material being withdrawn can be measured.

The device operates as follows.

Figure 3:
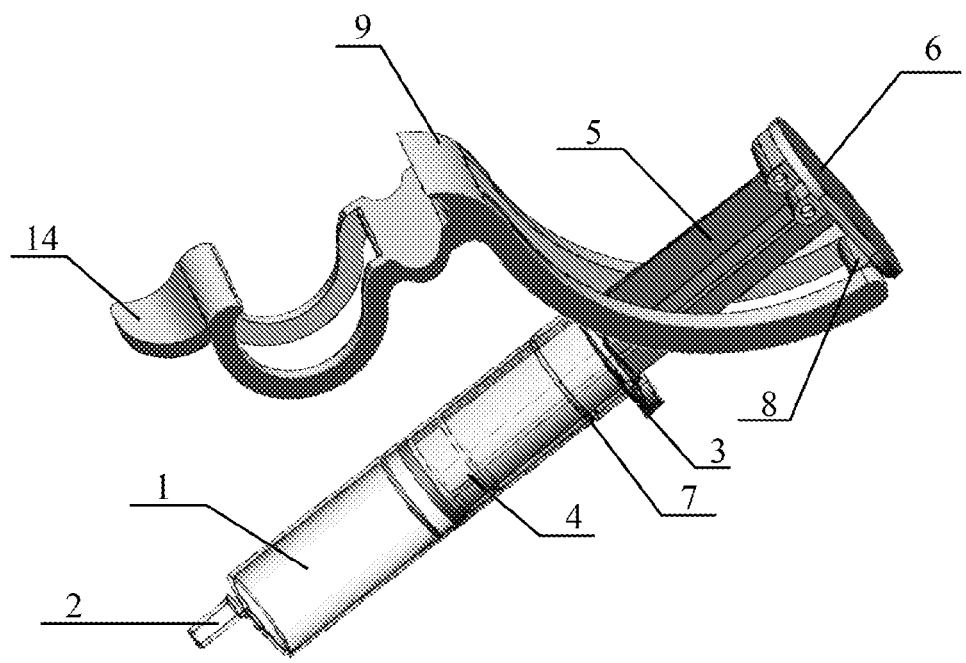
FIG. 3 shows a general view of the device in the process of performing aspiration.
Figure 4:
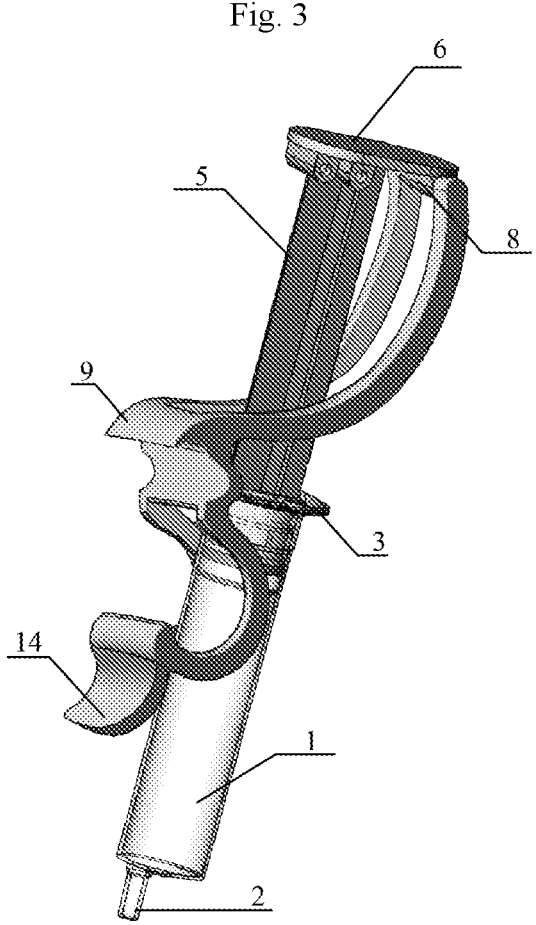
FIG. 4 shows a general view of the device with the handle maximally withdrawn.

After inserting the needle in the required area of the patient's body, a medical worker actuates the handle 9 with a movement of the thumb of the operating hand. The thumb engages the handle 9 (FIG. 3) and moves the reverse grip 11 toward the barrel 1 of the syringe, and while turning in it's the point it is attached to the grip 6 around the axis of the hinge unit 8 the bracket 10 engages the piston 5, which results in the piston 5 smoothly sliding out of the barrel 1, which in turn creates negative pressure in the barrel 1 of the syringe. Meanwhile, when engaging the handle 9, the operator moves the thumb toward the center of the palm clenching the hand, instead of retracting the thumb, which considerably lowers the load on the thumb joint and improves the operator's work comfort and productivity. With that, the rest of the fingers of the operating hand reliably hold the syringe to lower the risk of undesired movement of the needle and, thus, traumatizing the patient.

When the fingers are maximally clenched, the handle 9 abuts the barrel 1 of the syringe and the piston 5 moves to the top position creating negative pressure in the syringe, and aspiration is performed in the required volume. Since the position of the handle 9 is always controlled by the operator, aspiration stops when the pressure is taken off.

This syringe construction is particularly applicable to a syringe of small size, when the handle 9 is rather short and there is enough space for one finger.

In case of using a larger syringe (more than 10 ml) in order to ensure maximum movement of the arched bracket 10 and maximum displacement of the piston toward the topmost position while maintaining comfortable physiological grasp of the barrel and handle, the handle 9 with the auxiliary bracket 13 is used, the auxiliary bracket is formed with one or two concave (arched) elements and the tab 14, which are rests for the index, middle, and ring fingers (FIG.

4). Meanwhile, the barrel 1 enters the slot 15 of the bracket 13, and the tab 14 abuts the outer surface of the barrel 1.

When it is necessary to make an injection, one can move the fingers into a standard position and inject fluid by pressing the stem grip 6 with a thumb.

The disclosed device is convenient to use, ergonomic, lowers the load on the operator's hand and enhances productivity. The device is applicable in fields such as fine needle aspiration biopsy of various organs for the purpose of cytological diagnosis (all organs: liver, prostate gland, thyroid gland, mammary gland, and so on), aspiration of biomaterial (removing fluid: ascites, pleuritis, hemothorax, post operational seromas, hematomas at various sites, pus pockets, etc.), blood sampling, syringe liposuction, irrigation by medical substances (sinus infection, mastitis, abscessus, sclerotherapy of cysts at various sites, etc.), active (aspirational) wound drainage.

Furthermore, in addition to medical application, the disclosed device can be used in any other industry, such as chemical, food, and the like, and also in household for measured withdrawal of liquid preparations, especially if there is a measurement scale applied on the outer surface of the device.

What is claimed is:

1. An aspiration syringe comprising: a barrel with a tip for attaching a needle; a piston having a stem, the stem being slidably mounted inside the barrel; and a stem grip located at an end of the stem, wherein the syringe is provided with a handle moveably attached to the stem grip and rotatable in relation to a hinge unit located at the stem grip, wherein the handle is formed at least as a bracket with a reverse grip located at an end opposite to the handle attaching point, the handle further has a slot arranged in a middle portion of the bracket and configured to enclose the stem from two sides.

2. The syringe according to claim 1, wherein the stem grip is formed as an elongated pad extending asymmetrically in relation to an axis of symmetry of the stem, wherein the hinge unit is located on a bottom surface of the stem grip.

3. The syringe according to claim 1, wherein the bracket has an arched shape, wherein a radius of curvature of the bracket approximately equals a distance the piston exits the barrel in operation.

4. The syringe according to claim 3, wherein the slot in the bracket is formed along an entire length of the bracket, and a width of the slot corresponds to a diameter of the stem.

5. The syringe according to claim 1, wherein the handle is provided with an auxiliary bracket located on a bottom surface of the reverse grip.

6. The syringe according to claim 5, wherein the auxiliary bracket is formed as at least one arched element having a slot arranged in the middle portion of the auxiliary bracket and configured to enclose the barrel.

7. The syringe according to claim 5, wherein the auxiliary bracket is provided with a tab located at an end opposite to the reverse grip.

8. The syringe according to claim 6, wherein a width of the slot in the auxiliary bracket corresponds to an outer diameter of the barrel.

9. The syringe according to claim 7, wherein the auxiliary bracket is formed as two arched elements, the elements being coupled to each other and having different diameters, wherein the slot of the auxiliary bracket is formed only in the element of the bracket adjacent to the tab.

10. The syringe according to claim 9, wherein the two arched elements of the auxiliary bracket and the tab are formed so as to correspond to a plurality of fingers.

* * * * *